US005494892A

United States Patent [19]

Sprecker et al.

[11] Patent Number: 5,494,892

[45] Date of Patent: Feb. 27, 1996

[54] METHYL SUBSTITUTED PROPYL-SUBSTITUTED PENTAMETHYL INDANE DERIVATIVES PROCESSES FOR PRODUCING SAME AND PERFUMERY USES THEREOF

[75] Inventors: Mark A. Sprecker, Sea Bright; Olivier J. Gillotin, Denville, both of N.J.

[73] Assignee: International Flavors & Fragrances Inc., New York, N.Y.

[21] Appl. No.: 310,105

[22] Filed: Sep. 22, 1994

Related U.S. Application Data

[63] Continuation-in-part of Ser. No. 214,229, Mar. 17, 1994, Pat. No. 5,376,630.

[51] Int. Cl.$^6$ .................................................. A61K 7/46

[52] U.S. Cl. ............................ 512/14; 512/13; 568/659; 568/808; 549/385; 570/183

[58] Field of Search ............................ 570/183; 568/659, 568/808; 549/385; 512/13, 14

[56] References Cited

U.S. PATENT DOCUMENTS

| | | | |
|---|---|---|---|
| 3,660,311 | 5/1972 | Wight | 252/522 |
| 4,001,330 | 1/1977 | Curran | 568/808 |
| 4,162,256 | 7/1979 | Sprecker et al. | 549/385 |
| 4,292,193 | 9/1991 | Wiegers et al. | 512/14 |
| 4,314,915 | 2/1981 | Wiegers et al. | 512/14 |
| 5,250,200 | 2/1981 | Wiegers et al. | 512/14 |
| 5,376,630 | 12/1994 | Sprecker et al. | 512/13 |

*Primary Examiner*—James H. Reamer
*Attorney, Agent, or Firm*—Arthur L. Liberman

[57] ABSTRACT

Described are methyl, substituted propyl-substituted pentamethyl indane derivatives defined according to the structure:

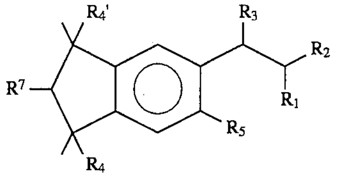

wherein $R_1$ represents hydroxyl or methyl; and $R_2$ represents hydrogen, chloro or $OR_6$; and $R_3$ represents hydrogen or methyl with the provisos:

(i) when $R_1$ is hydroxyl, $R_2$ is hydrogen and $R_3$ is methyl; and (ii) when $R_1$ is methyl, one of $R_2$ is chloro or $OR_6$ and $R_3$ is hydrogen
augmenting, enhancing or imparting aromas in or to perfume compositions, colognes and perfumed articles including but not limited to solid or liquid anionic, cationic, nonionic or zwitterionic detergents, perfumed polymers, fabric softener compositions, fabric softener articles, cosmetic powders and hair preparations.

Also described are processes for preparing such methyl, substituted propyl-substituted pentamethyl indane derivatives using as a starting material the mixture of compounds defined according to the structure:

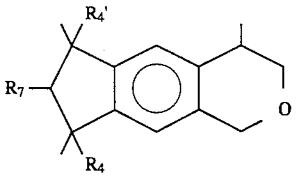

also know as GALAXOLIDE® (trademark of International Flavors & Fragrances Inc.).

19 Claims, 5 Drawing Sheets

FIG. I

NMR SPECTRUM FOR EXAMPLE I.

GLC PROFILE FOR EXAMPLE II.

NMR SPECTRUM FOR EXAMPLE II.

NMR SPECTRUM FOR EXAMPLE III.

FIG. 5
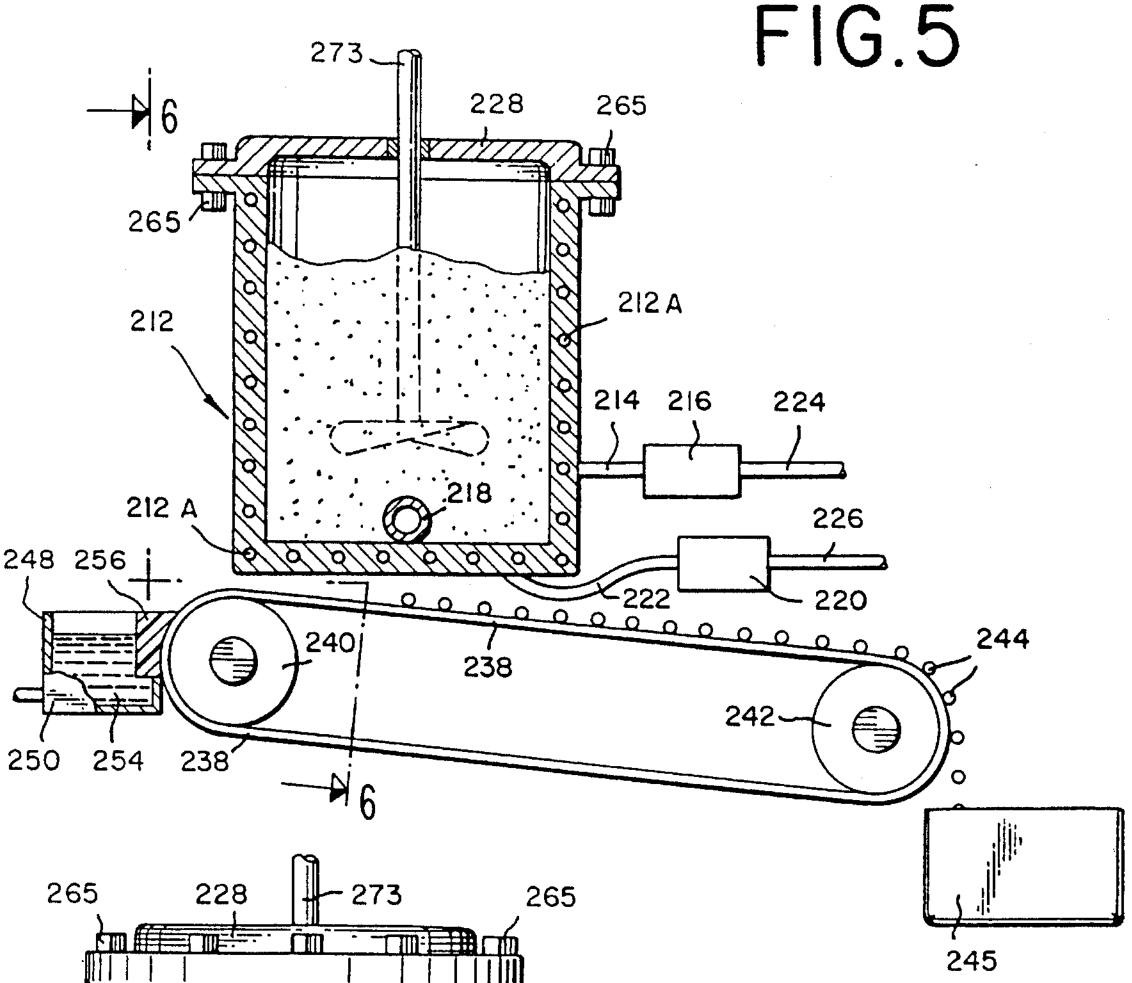
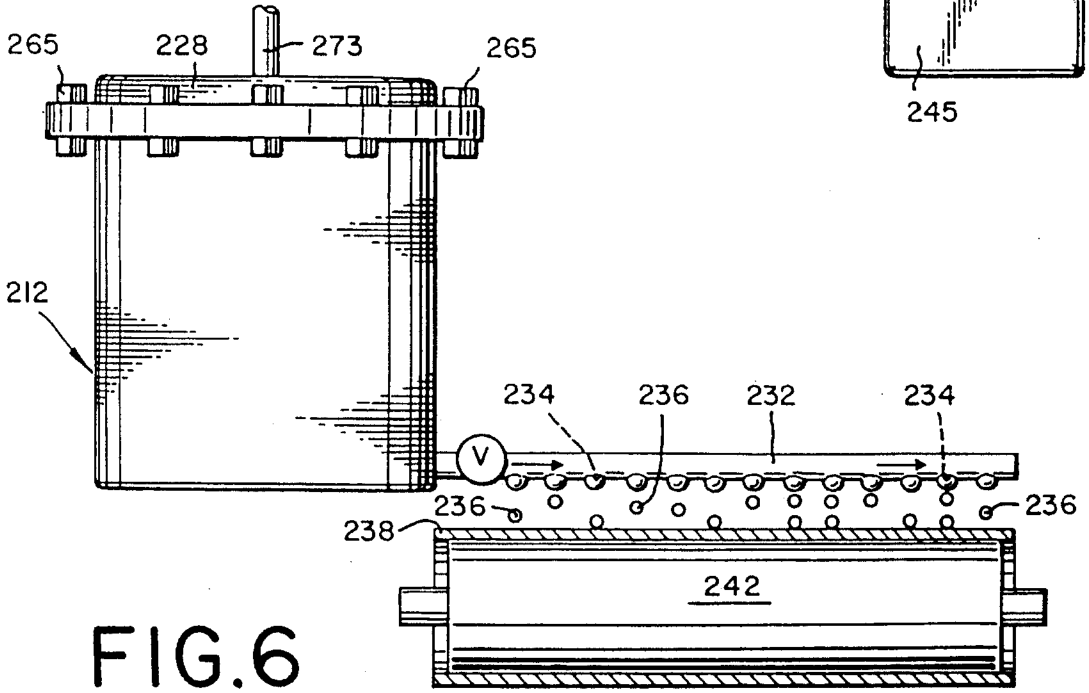
FIG. 6

METHYL SUBSTITUTED PROPYL-SUBSTITUTED PENTAMETHYL INDANE DERIVATIVES PROCESSES FOR PRODUCING SAME AND PERFUMERY USES THEREOF

This application is a CIP of application Ser. No. 214,229 filed Mar. 17, 1994 U.S. Pat. No. 5,376,630.

BACKGROUND OF THE INVENTION

The present invention relates to methyl, substituted propyl-substituted pentamethyl indane derivatives defined according to the structure:

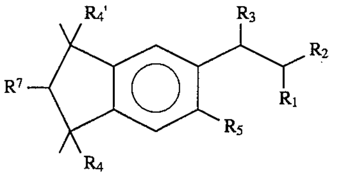

wherein $R_1$ represents hydroxyl or methyl; $R_2$ represents hydrogen, chloro or $OR_6$ and $R_3$ represents hydrogen or methyl with the provisos that:

(i) when $R_1$ is hydroxyl, $R_2$ is hydrogen and $R_3$ is methyl; and (ii) when $R_1$ is methyl, one of $R_2$ is chloro or $OR_6$ and $R_3$ is hydrogen wherein $R_6$ is methyl, ethyl, n-propyl or i-propyl and wherein the structure represents a mixture wherein in the mixture in one of the compounds $R_4$ and $R_4'$ are both methyl and $R_7$ is methyl; and in the other compounds one of $R_4$ or $R_4'$ is methyl and the other is ethyl and $R_7$ is hydrogen and organoleptic uses thereof in augmenting, enhancing or imparting aroma nuances in or to perfume compositions, perfumed articles and colognes.

There has been considerable work performed relating to substances which can be used to impart (to alter, modify or enhance) fragrances to (or in) various consumable materials. These substances are used to diminish the use of natural materials some of which may be in short supply and to provide more uniform properties in the finished product. Musky aromas are highly desirable in several types of perfume compositions and for use in perfumed articles Natural "musky" aromas are highly sought after and heretofore have been virtually impossible to duplicate. Accordingly, a need exists in the perfume art to duplicate as closely as possible natural musky aroma nuances.

Oxygenated indane derivatives such as those having the structure:

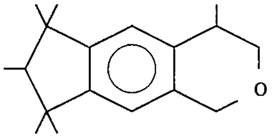

and having the structure:

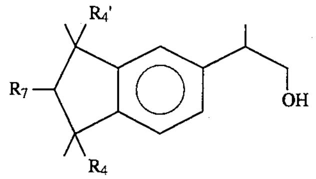

are known in the prior art to give rise to musk aromas. Thus, U.S. Pat. Nos. 3,660,311 of May 2, 1972 and 4,162,256 of Jul. 24, 1979 disclose the perfumery use of the compound having the structure:

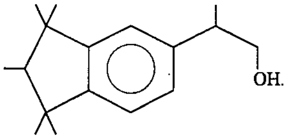

Furthermore, the compound having the structure:

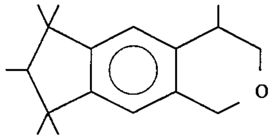

is disclosed as having musk aromas in the following U.S. Patents:

U.S. Pat. No. 3,360,530 issued on Dec. 26, 1967;
U.S. Pat. No. 4,295,978 issued on Oct. 20, 1981; and
U.S. Pat. No. 4,650,603 issued on Mar. 17, 1987.

Furthermore, processes for the production of such materials are set forth in:

U.S. Pat. No. 3,532,719;
U.S. Pat. No. 3,910,964; as well as:
U.S. Pat. No. 3,978,090.

Nothing in the prior art, however, discloses the unobvious, unexpected and advantageous properties of the methyl, substituted propyl-substituted pentamethyl indane derivatives of our invention; and nothing in the prior art discloses the unexpected, advantageous techniques of preparing the methyl, substituted propyl-substituted pentamethyl indane derivatives of our invention via the newly discovered rearrangement reaction set forth in detail and exemplified, infra.

RELATED CO-PENDING APPLICATIONS

This Application is a continuation in part of Application for U.S. Letters Patents Ser. No. 08/214,229 filed on Mar. 17, 1994.

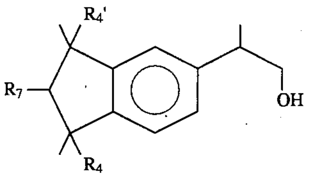

prepared according to Example I.

Figure 2:
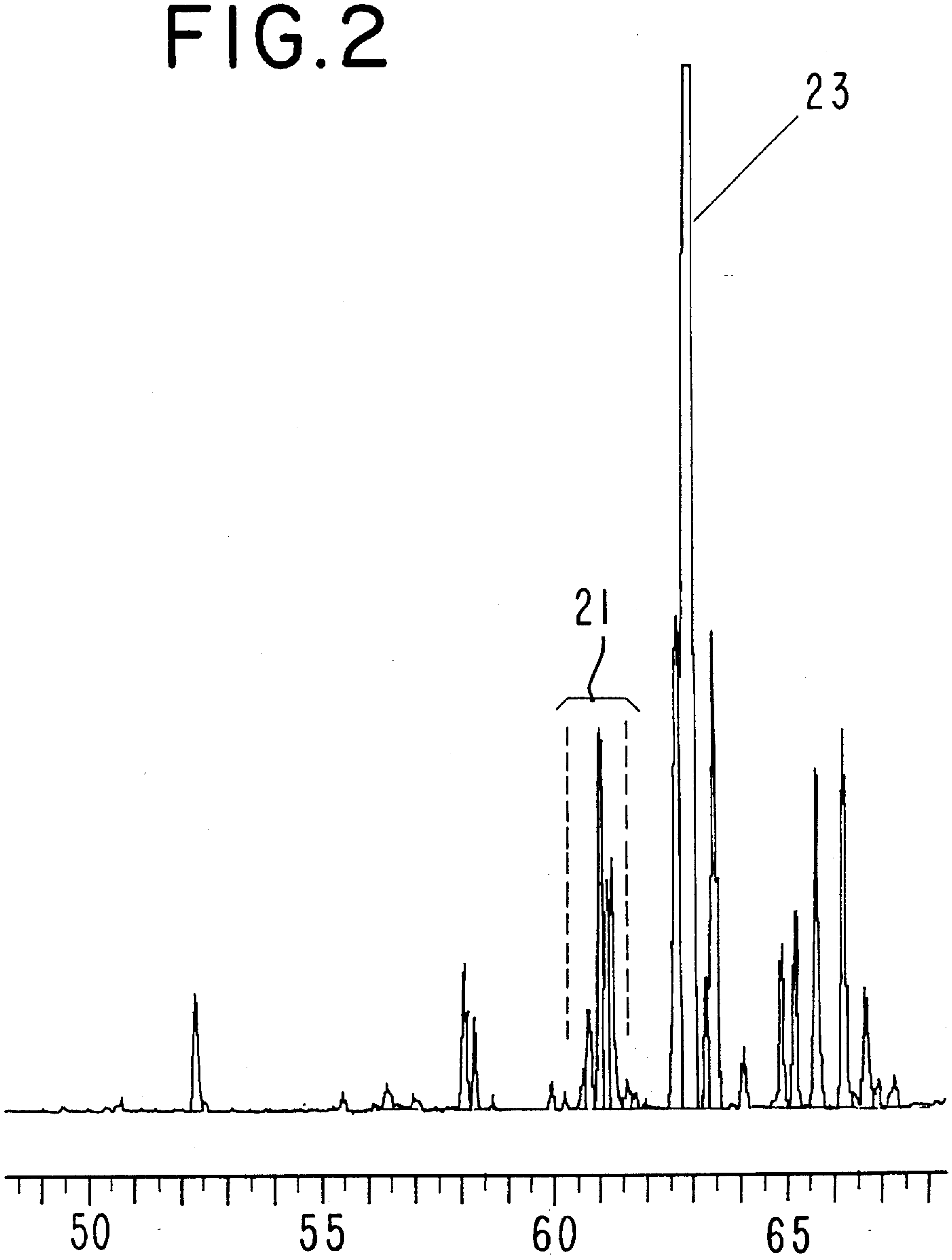

FIG. 2 is the GLC profile for the mixture of compounds defined according to the structure:

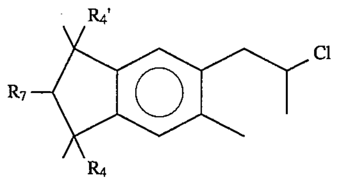

prepared according to Example II wherein the structure represents a mixture wherein, in the mixture in one of the compounds $R_4$ and $R_4'$ are both methyl and $R_7$ is methyl; and in the other compounds one of $R_4$ or $R_4'$ is methyl and the other is ethyl and $R_7$ is hydrogen (Conditions: 50 meter ×0.32 mm bonded methyl silicone column programmed from 75° C.–225° C. at 2° C. per minute).

Figure 3:
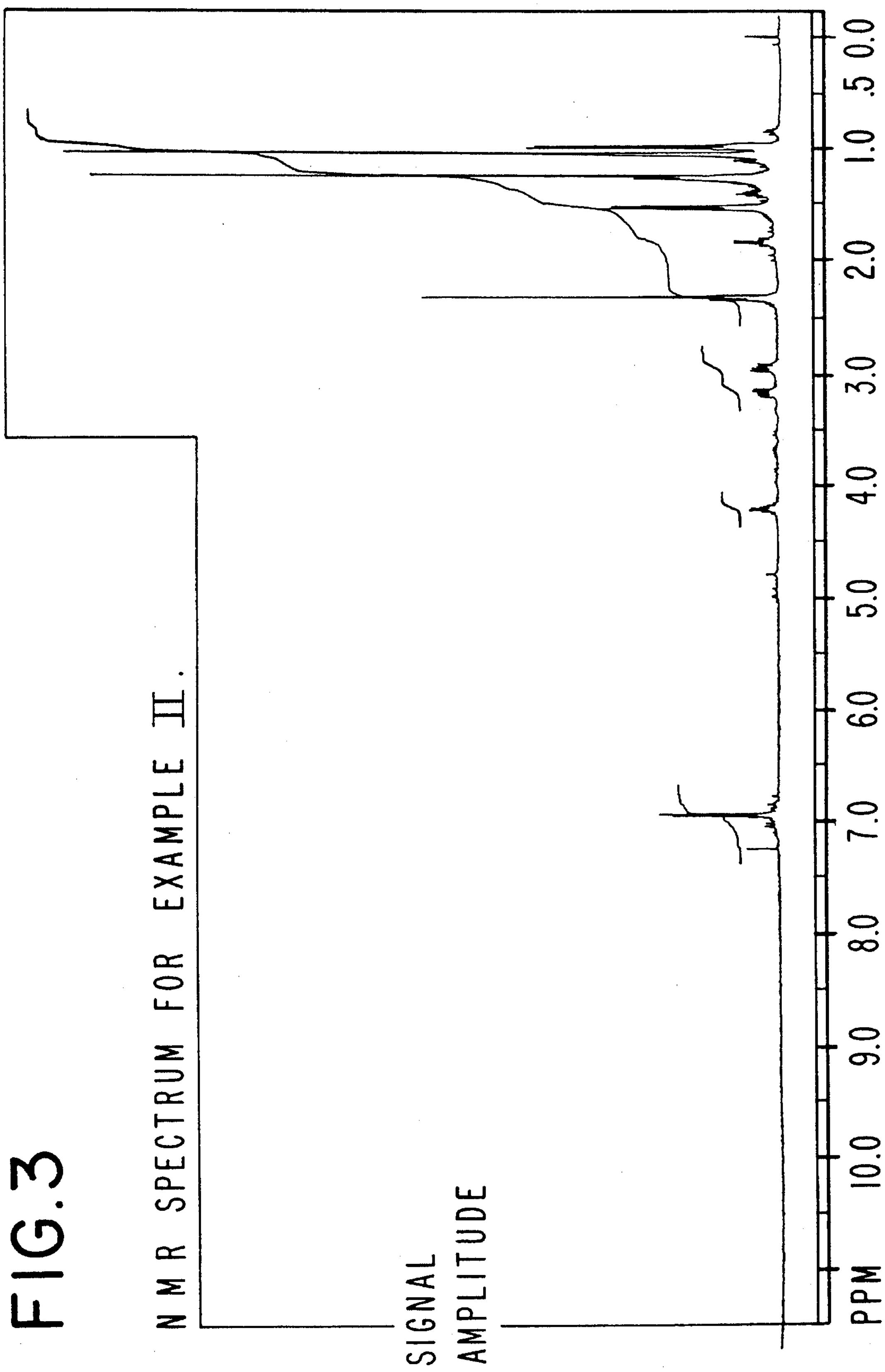

FIG. 3 is the NMR spectrum for the compound having the structure:

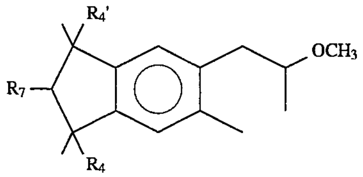

prepared according to Example II.

Figure 4:
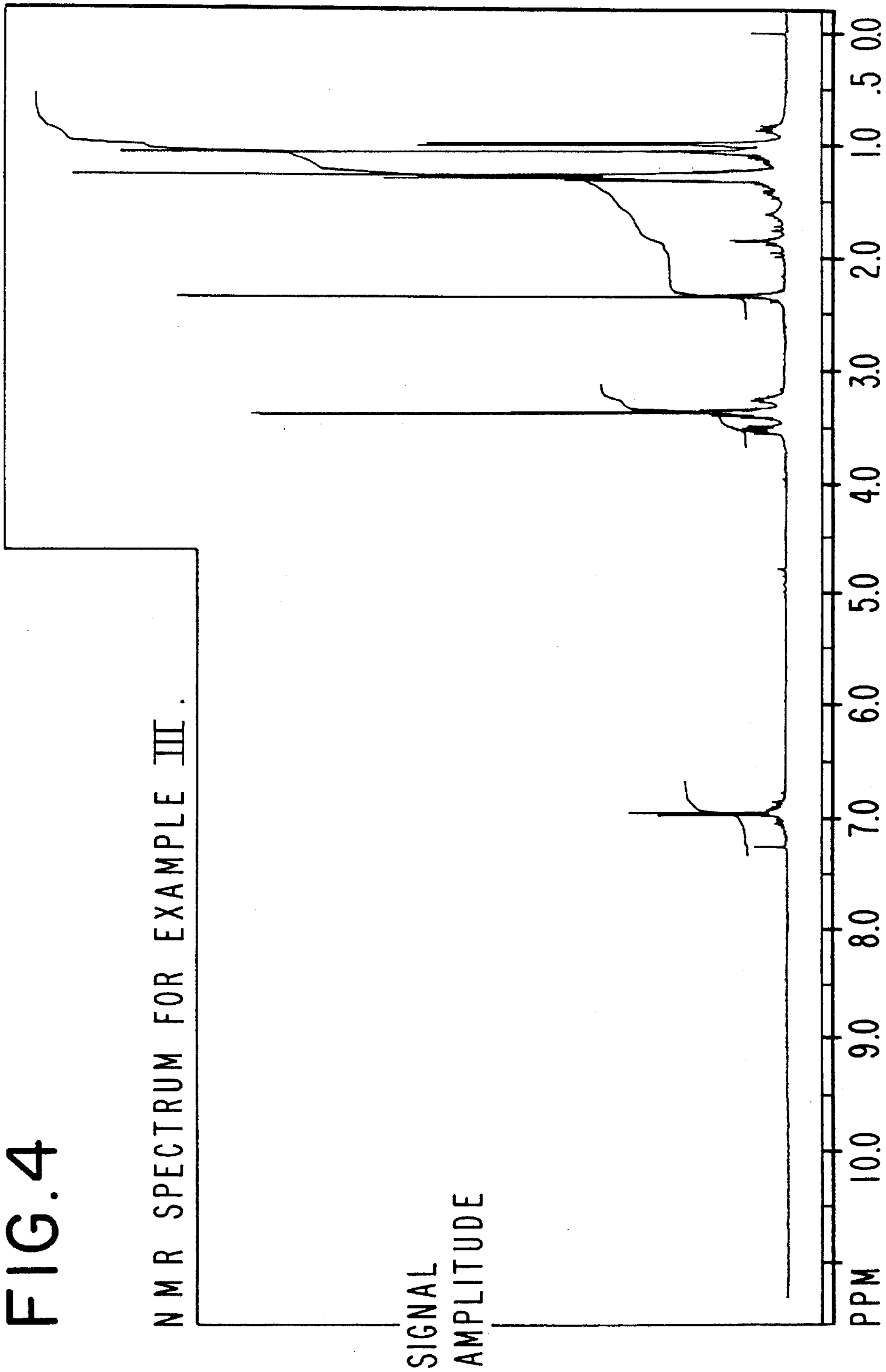

FIG. 4 is the MNR spectrum for the mixture of compounds defined according to the structure:

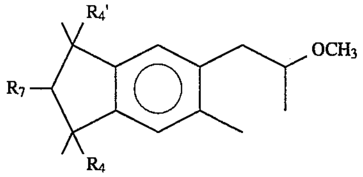

prepared according to Example III wherein the structure represents a mixture, wherein in the mixture, in one of the compounds $R_4$ and $R_4'$ are both methyl and $R_7$ is methyl; and in the other compounds one of $R_4$ or $R_4'$ is methyl and the other is ethyl and $R_7$ is hydrogen.

FIG. 5 represents a cut-away side elevation view of apparatus used in forming perfumed polymers which contain imbedded in the interstices thereof at least one of the methyl, substituted propyl-substituted pentamethyl indane derivatives of our invention.

FIG. 6 is a front view of the apparatus of FIG. 5 in the direction of the arrows.

DETAILED DESCRIPTION OF THE DRAWINGS

Referring to FIG. 2, FIG. 2 is a GLC profile for the reaction product of Example II. The peaks indicated by reference numeral 21 are peaks for the compounds having the structure:

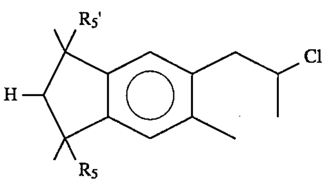

wherein the structure represents a mixture, wherein in the mixture one of $R_5$ or $R_5'$ is methyl and the other of $R_5$ or $R_5'$ is ethyl. The peak indicated by reference numeral 23 is the peak for the compound having the structure:

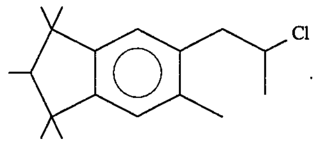

Referring to FIGS. 5 and 6, there is provided a process for forming scented polymer elements (wherein the polymer may be a thermoplastic polymer such as a low density polyethylene or polypropylene or copolymers of ethylene-vinyl acetate or mixtures of a polymer and copolymer such as a copolymer of ethylene-vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. Their lower-most portion of the container is maintained at a slightly lower temperature and the material in the container is taken off at such location for delivery through the conduit. Thus, referring to FIGS. 5 and 6, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and a perfuming substance containing at least one of the methyl, substituted propyl-substituted pentamethyl indane derivatives of our invention is placed. The container is closed by means of an air-tight lid 228 and clamped to the container by bolts 265. A stirrer 273 traverses the lid or cover 228 in an air-tight manner and is rotatable in a suitable manner.

A surrounding cylinder 212 having heating coils 212A which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater is operated to maintain the upper portion of the container 212 within a temperature range of, for example, 250°–270° C. in the case of low density polyethylene.

The bottom portion of the container 212 is heated by means of heating coils 212A regulated through the control 220 connected thereto through a connecting wire 222 to maintain the lower portion of the container 212 with a temperature range of 225°–240° C.

Thus, the polymer or mixture of polymers added to the container 212 is heated from 10–12 hours, whereafter the perfume composition or perfume material containing at least one of the methyl, substituted propyl-substituted pentamethyl indane derivatives of our invention is quickly added to the melt. Generally, about 10–45% by weight of the resulting mixture of perfumery substance is added to the polymer.

After the perfume material is added to the container 212, the mixture is stirred for a few minutes, for example, 5–15 minutes and maintained within the temperature ranges indicated previously by the heating coils 212A. The controls 216 and 220 are connected through cables 224 and 226 to a suitable supply of electrical current for supplying the power for heating purposes.

Thereafter, the valve "V" is opened permitting the mass to flow outwardly through conduit 232 (also indicated by pipe 218) having a multiplicity of orifices 234 adjacent to the lower side thereof. The outer end of the conduit 232 is closed so that the liquid polymer intimately admixed with at least one of the methyl, substituted propyl-substituted pentamethyl indane derivatives of our invention will continuously drop through the orifices 234 downwardly from the conduit 232. During this time, the temperature of the polymer intimately admixed with the perfumery substance in the container 212 is accurately controlled so that a temperature in the range of from about 240°–250° C. (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance containing at least one of the methyl, substituted propyl-substituted pentamethyl indane derivatives of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for formation of other functional products, e.g., garbage bags and the like.

THE INVENTION

Our invention relates to methyl, substituted propyl-substituted pentamethyl indane derivatives defined according to the generic structure:

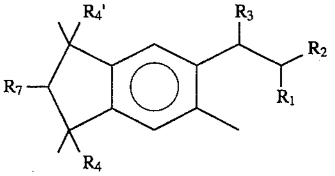

wherein $R_1$ represents hydroxyl or methyl; $R_2$ represents hydrogen, chloro or $OR_6$; and $R_3$ represents hydrogen or methyl with the provisos:

(i) when $R_1$ is hydroxyl, $R_2$ is hydrogen and $R_3$ is methyl; and (ii) when $R_1$ is methyl, one of $R_2$ is chloro or $OR_6$ and $R_3$ is hydrogen wherein $R_6$ methyl, ethyl, n-propyl or i-propyl and wherein the structure represents a mixture wherein, in the mixture in one of the compounds $R_4$ and $R_4'$ are both methyl and $R_7$ is methyl; and in the other compounds one of $R_4$ or $R_4'$ is methyl and the other of $R_4$ or $R_4'$ is ethyl and $R_7$ is hydrogen.

Our invention also relates to mixtures of such methyl, substituted propyl-substituted pentamethyl indane derivatives with other musk chemicals including those defined according to the structures:

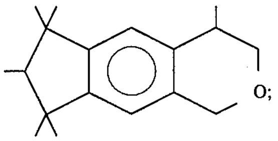

-continued

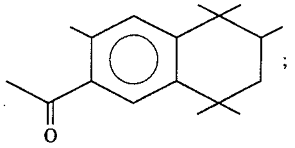

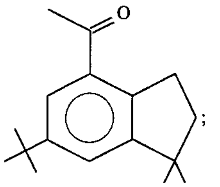

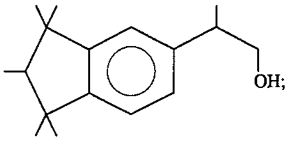

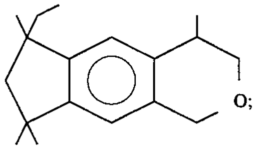

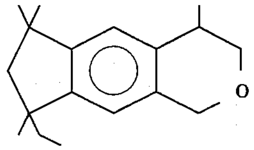

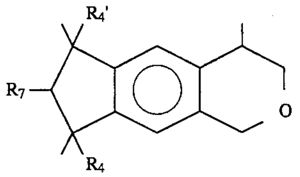

wherein the structure:

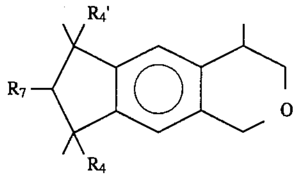

represents a mixture wherein, in the mixture in one of the compounds $R_4$ and $R_4'$ are both methyl and $R_7$ is methyl (about 90% of the mixture by weight); and in the other compounds one of $R_4$ or $R_4'$ is methyl and the other of $R_4$ or $R_4'$ is ethyl and $R_7$ is hydrogen (about 10% by weight of the compounds).

Our invention is also intended to define processes for preparing methyl substituted propyl-substituted pentamethyl indane derivatives defined according to the structure:

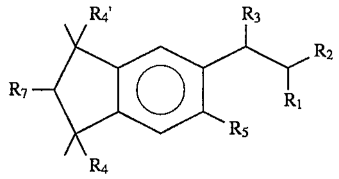

by means of first hydrogenating compounds defined according to the structure:

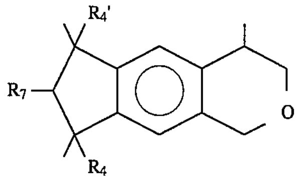

in the presence of a palladium-type catalyst according to the reaction:

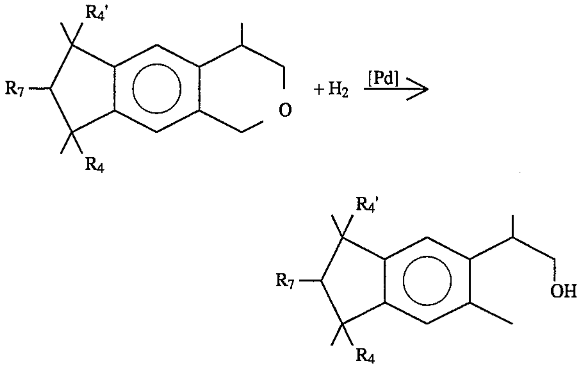

whereby the mixture of compounds having the structure:

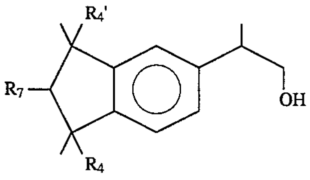

is produced. The hydrogenation reaction takes place at 80°–150° C. at a pressure of 100–500 pounds per square inch using a palladium-type catalyst, that is , palladium suspended on carbon (preferably about 5% palladium suspended on carbon) or palladium suspended on aluminum oxide (preferably 5% palladium suspended on aluminum oxide) or palladium trichloride further in the presence of an acid catalyst (preferably phosphoric acid or an acid clay, e.g., FILTROL® acid clay (trademark of Engelhardt Corp. of Iselin, N.J.). The amount of "palladium" catalyst is 1–4% of the reaction mass. The amount of additional acid catalyst is 1–4% of the reaction mass.

At the end of the reaction, the reaction product can be used as is for its organoleptic properties and can be combined with such compounds as the compound having the structure:

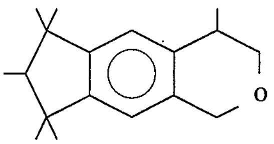

or the compound having the structure:

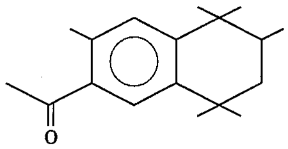

or the compound having the structure:

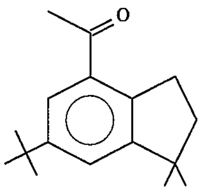

or the compound having the structure:

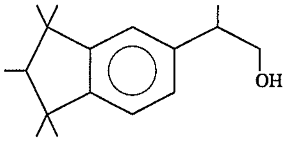

preferably in an amount of from about 1 up to about 10% by weight of the compound mixture having the structure

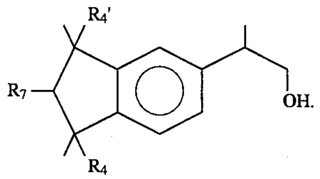

On the other hand, the mixture of compounds having the structure:

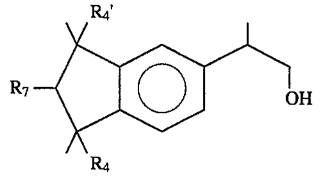

can further be reacted with a "chlorinating-rearrangement" reagent which would give rise to the mixture of compounds having the structure:

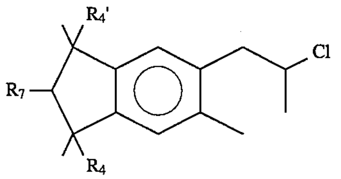

according to the reaction:

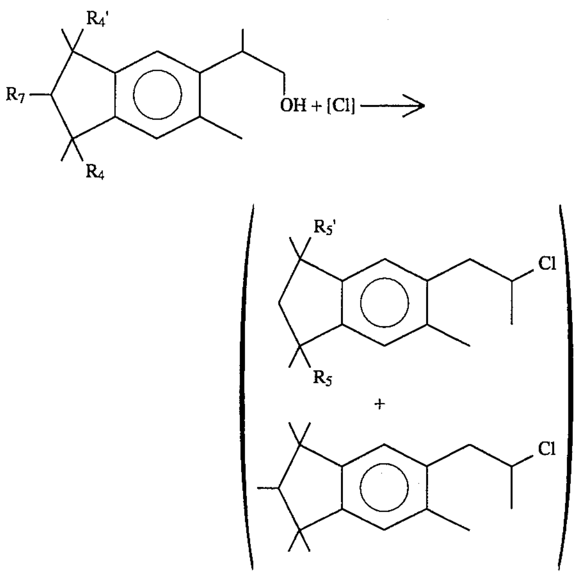

Examples of the chlorinating compound, to wit:

“[Cl]”

are:

$SOCl_2$;
$PCl_3$;
$PCl_5$; and
$POCl_3$.

This reaction must take place in the presence of a chlorinated Lewis acid catalyst which is preferably one of:

$SnCl_4$;
$TiCl_4$;
$AlCl_3$;
Diethyl aluminum chloride; and
Ethyl aluminum dichloride.

The amount of Lewis acid catalyst may vary from about 1–20% by weight of the reaction mass. The temperature of reaction may vary from about 0° C. up to about 100° C.

Higher temperatures of reaction will give rise to shorter times of reaction. An example of this reaction is set forth in Example II, infra, and is as follows:

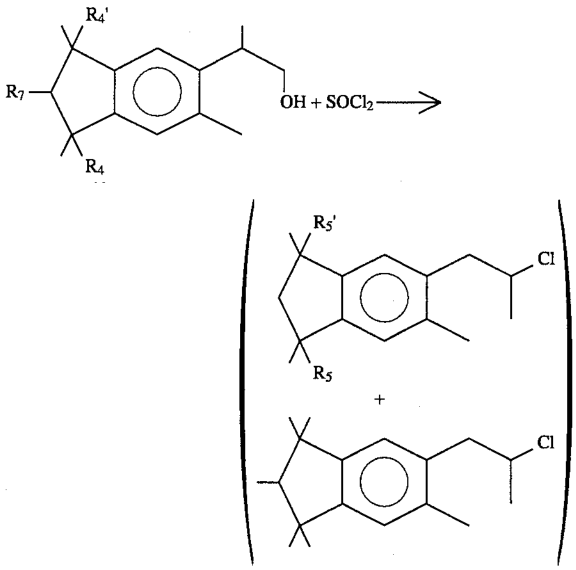

wherein the compound mixture, to wit:

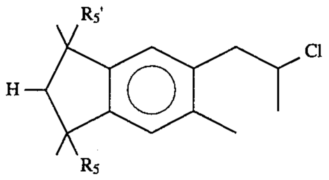

is one wherein one of $R_5$ or $R_5'$ is methyl and the other of $R_5$ or $R_5'$ is ethyl.

The rearrangement mechanism of this reaction, exemplified with using $SnCl_4$ as a Lewis acid catalyst is as follows:

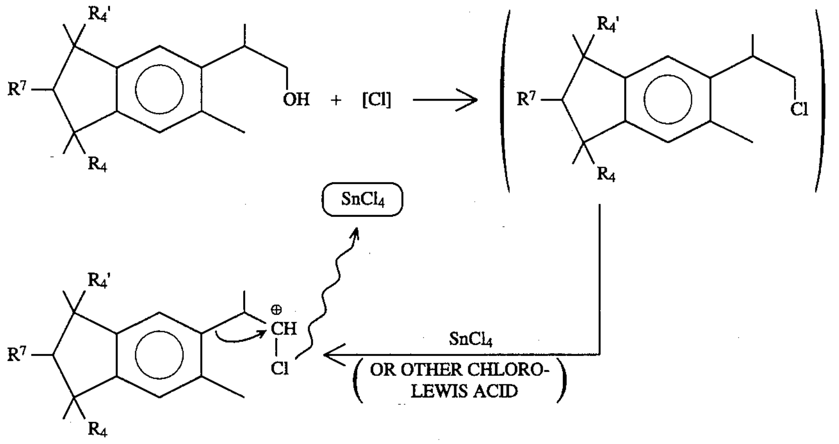

-continued

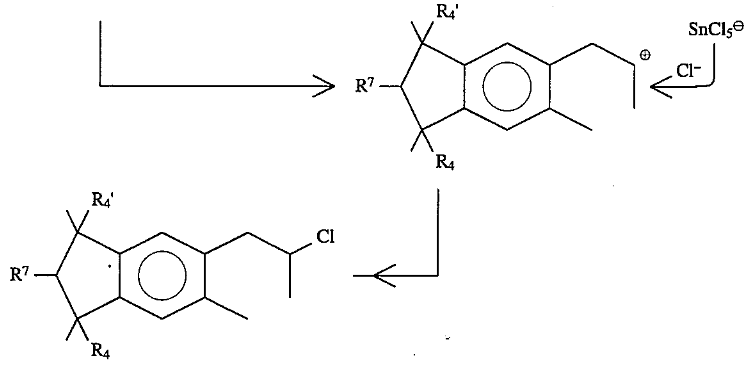

The resulting mixture of compounds is then fractionally distilled and either may be utilized for its organoleptic properties or may be further reacted. Thus, the mixture of compounds defined according to the structure:

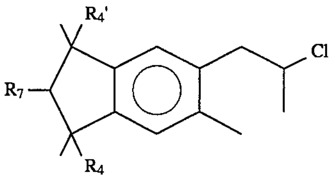

may further be reacted with a metal alkoxide defined according to the formula:

$$M(OR_6)_x$$

wherein M is a metal selected from the group consisting of sodium, lithium, potassium, aluminum and titanium and $R_6$ represents methyl, ethyl, isopropyl or n-propyl; and wherein x is the valence of the metal M (for example, 3 in the case of aluminum; 4 in the case of titanium; and 1 in the case of sodium). Thus, x is defined as an integer from 1 up to 4. The reactions are generically shown, thusly:

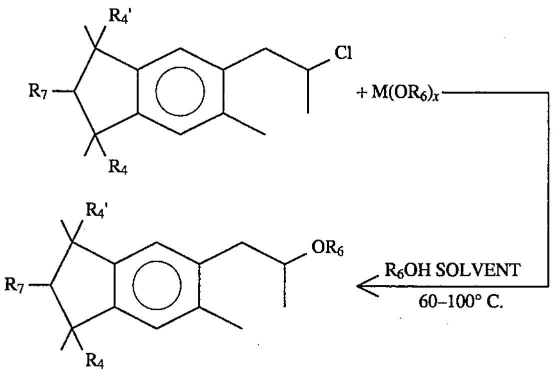

This reaction is carried out at a temperature in the range of from 60° C. up to 100° C. using a $R_6OH$ solvent. Thus, for example, when sodium methoxide is used as a reaction ingredient, methyl alcohol is the solvent and the temperature is between 60° C. and 70° C. as exemplified by means of the following reaction:

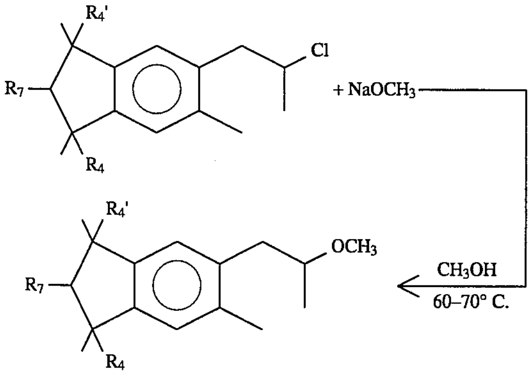

which is further exemplified in Example III, infra.

The following table sets forth exemplary reaction products, exemplary mixtures of reaction products with other musk chemicals and organoleptic properties of such substances.

TABLE I

| Methyl, substituted propyl-substituted pentamethyl indane derivative or methyl, substituted propyl-substituted pentamethyl indane derivative containing substance | Organoleptic Properties |
|---|---|
| Mixture of compounds defined according to the structure: 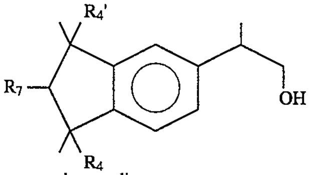 prepared according to Example I. | An intense natural musky aroma. |
| Mixture of compounds defined according to the structure: 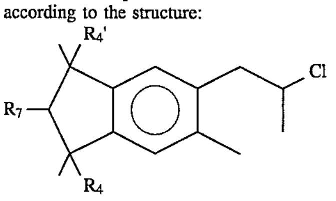 prepared according to Example II. | An intense, natural woody musk, aroma with pleasant natural animalic topnotes. |
| Mixture of compounds defined | A natural musk, |

TABLE I-continued

| Methyl, substituted propyl-substituted pentamethyl indane derivative or methyl, substituted propyl-substituted pentamethyl indane derivative containing substance | Organoleptic Properties |
|---|---|
| according to the structure: 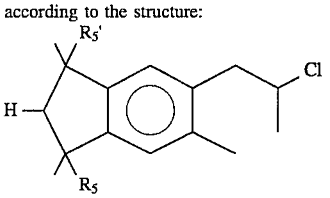 | rose-like aroma with green undertones and lilac topnotes. |
| 3% Mixture of the compounds defined according to the structure: 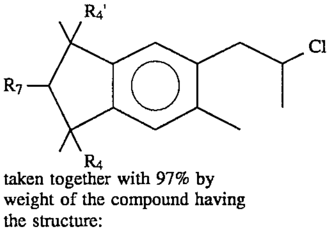 taken together with 97% by weight of the compound having the structure: 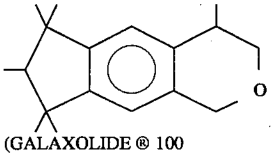 (GALAXOLIDE ® 100 (trademark of International Flavors & Fragrances Inc.) | An intense powdery sweet natural musk aroma with woody topnotes. |
| 3% Mixture of the compounds having the structure: 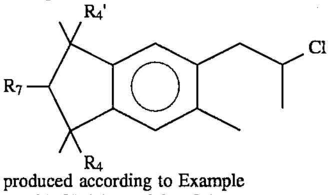 produced according to Example II with 97% by weight of the compound having the structure: 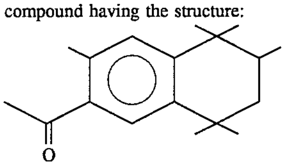 | An intense powdery sweet natural musk with animalic topnotes. |
| 7% Mixture containing the compound mixture having the structure: 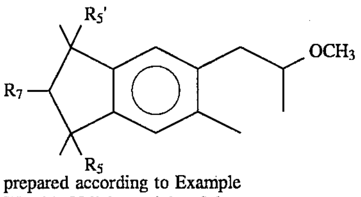 prepared according to Example III with 93% by weight of the compound having the structure: 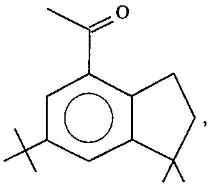, | An intense powdery sweet natural musk aroma with woody, mahogany, green undertones and faint lilac topnotes. |

The methyl, substituted propyl-substituted pentamethyl indane derivatives of our invention and if desired, an additional musk chemical as set forth, supra, and if desired, one or more auxiliary perfume ingredients, including, for example, hydrocarbons, alcohols (other than the alcohols of our invention), ketones, aldehydes, nitriles, esters, lactones, ethers (other than the ethers of our invention), hydrocarbons, chlorinated derivatives (other than the chlorinated derivatives of our invention), synthetic essential oils and natural essential oils may be admixed so that the combined odors of the individual components produce a pleasant and desired fragrance particularly and preferably in the musk fragrance area. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the overall sensory effect of the perfume composition will be at least the sum total of the effects of each of the ingredients. Thus, one or more of the methyl, substituted propyl-substituted pentamethyl indane derivatives of our invention taken alone or further together with a musk chemical such as the compound having the structure:

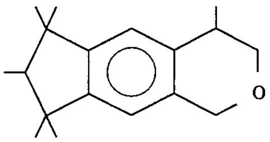

can be used to alter, modify or enhance the aroma characteristics of a perfume composition, for example, by tuilizing or moderating the olfactory reaction contributed by another ingredient in the composition.

The amount of the methyl, substituted propyl-substituted pentamethyl indane derivatives of our invention which will be effective in perfume compositions as well as in perfumed articles and colognes depends upon many factors, including the other ingredients (e.g., other musk chemicals such as the compounds having the structures:

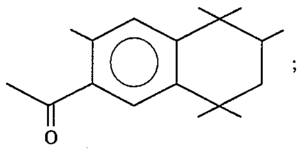

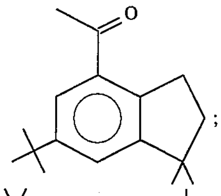

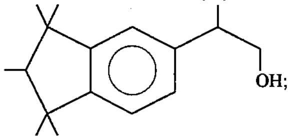

and

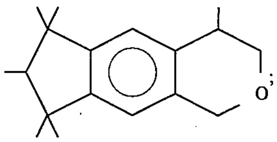

their amounts and the effects which are desired. It has been found that perfume compositions containing as little as 0.0005% of one or more of the methyl, substituted propyl-substituted pentamethyl indane derivatives of our invention or even less (e.g., 0.002%) can be used to impart intense, substantive, natural musk, natural woody, rose-like and powdery sweet aromas with animalic, woody and lilac topnotes and green, woody and mahogany undertones to soaps, cosmetics, detergents (including anionic, cationic, nonionic or zwitterionic solid or liquid detergents) or other products. The amount employed can range up to 100% of the fragrance components and will depend upon ii considerations of cost, nature of the end product, the effect desired on the finished product and the particular fragrance sought.

The methyl, substituted propyl-substituted pentamethyl indane derivatives of our invention taken alone or further together with other musk chemicals including the compounds having the structures:

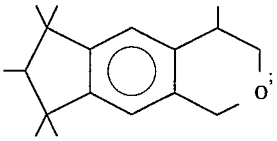

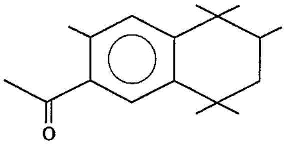

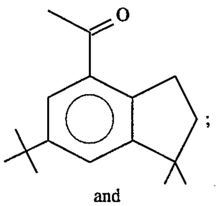

and

-continued

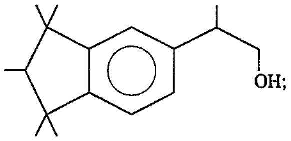

are useful (taken alone or together with other ingredients in perfume compositions), in detergents and soaps, space odorants and deodorants, perfumes, colognes, toilet water, bath preparations such as lacquers, brilliantines, pomades and shampoos, cosmetic preparations such as creams, deodorants, hand lotions and sun screens; powders, such as talcs, dusting powders, face powders and the like.

As little as 0.7% of at least one of the methyl, substituted propyl-substituted pentamethyl indane derivatives of our invention will suffice to impart an intense and substantive natural musk, natural woody, rose-like and powdery sweet aroma with animalic, woody and lilac topnotes and green, woody and mahogany undertones to musk perfume formulations. Generally, no more than 5% of at least one of the methyl, substituted propyl-substituted pentamethyl indane derivatives of our invention based on the ultimate end product is required to be used "as is" or in the perfume composition.

Furthermore, as little as 0.25% of one or more of the methyl, substituted propyl-substituted pentamethyl indane derivatives of our invention taken alone or further together with another musk chemical such as the compound having the structure:

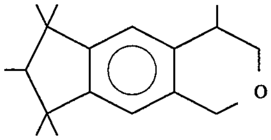

will suffice to impart such aroma to perfumed articles per se, whether in the presence of other perfume materials or whether used by themselves. Thus, the range of use of the methyl, substituted propyl-substituted pentamethyl indane derivatives of our invention in perfumed articles may vary from about 0.25% up to about 5% by weight based on the total weight of the perfumed article.

In addition, the perfume composition or fragrance composition of our invention can contain a vehicle, or carrier for at least one of the methyl, substituted propyl-substituted pentamethyl indane derivatives of our invention taken alone or together with another musk chemical such as the compound having the structure:

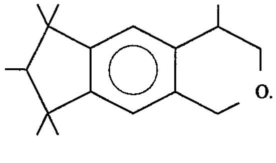

The vehicle can be a liquid such as a non-toxic alcohol, e.g., ethanol, a non-toxic glycol, e.g., propylene glycol or the like. The carrier can also be an absorbent solid, such as a gum (e.g., gum arabic), or components for encapsulating the composition by means of coacervation (such as gelatin).

It will thus be apparent that at least one of the methyl, substituted propyl-substituted pentamethyl indane derivatives of our invention taken alone or further together with another musk chemical such as a musk chemical having one of the structures:

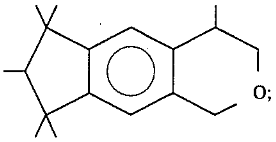

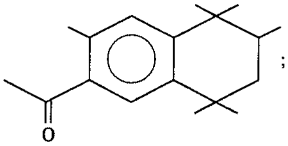

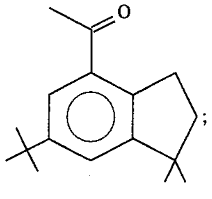

and/or

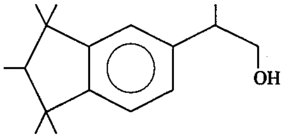

can be utilized to alter, modify or enhance the aroma of perfume compositions, colognes or perfumed articles.

The following Examples I, II and III serve to illustrate processes for producing the methyl, substituted propylsubstituted pentamethyl indane derivatives of our invention. Examples following Example III in general, serve to illustrate organoleptic utilities of the methyl, substituted propyl-substituted pentamethyl indane derivatives of our invention or mixtures of methyl, substituted propyl-substituted pentamethyl indane derivatives with other musk materials.

In general, the following examples serve to illustrate specific embodiments of our invention. It will be understood that these examples are illustrative and that the invention is to be considered restricted thereto only as indicated in the appended claims.

All parts and percentages given herewith are by weight unless otherwise specified.

EXAMPLE I

PREPARATION OF "METHYL GALAXOLIDE® ALCOHOL"

Reaction:

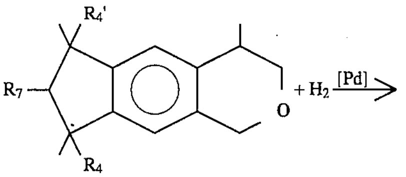

-continued

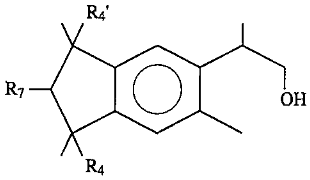

wherein, the materials represented by the structures:

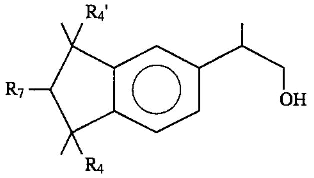

and

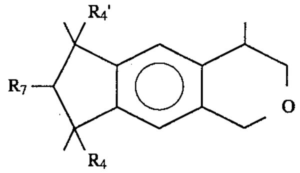

these materials are mixtures wherein, in the mixtures in one of the compounds $R_4$ and $R_4'$ are both methyl and $R_7$ is methyl (90% of the mixture) and in the other compounds one of $R_4$ or $R_4'$ is methyl and the other is ethyl and $R_7$ is hydrogen (10% of the mixture of compounds).

Into a 1 liter pressurized autoclave are placed 400 grams of the mixture of compounds having the structure:

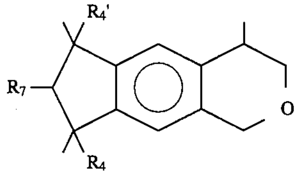

(wherein, in the mixture in one of the compounds $R_4$ and $R_4'$ are both methyl and $R_7$ is methyl (90% of the mixture) and in the other compounds one of $R_4$ or $R_4'$ is methyl and the other is ethyl and $R_7$ is hydrogen (10% of the mixture of compounds); 80% of isopropyl alcohol; 4 grams of FILTROL 13® (acid clay marketed by Engelhardt Corporation of Iselin, N.J.) and 2 grams of 5% palladium supported on carbon catalyst.

The autoclave is sealed and pressurized to 600 pounds per square inch using pressurized hydrogen and maintained at a temperature of about 130°–135° C. for a period of 4.5 hours. The temperature is then raised to 145°–150° C. for a period of 7.5 hours.

The autoclave is then cooled to room temperature and opened and the contents are filtered. The resulting product is then worked up and fractionally crystallized yielding the mixture compounds defined according to the structure:

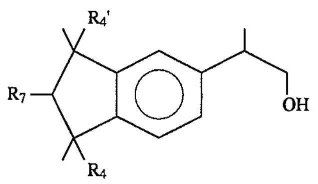

wherein, in the mixture in one of the compounds $R_4$ and $R_4'$ are both methyl and $R_7$ is methyl (90% by weight of the mixture) and in the other compounds one of $R_4$ or $R_4'$ is methyl and the other of $R_4$ or $R_4'$ is ethyl and $R_7$ is hydrogen (10% by weight of the mixture) .

The resulting product has an intense and natural musky aroma.

Figure 1:
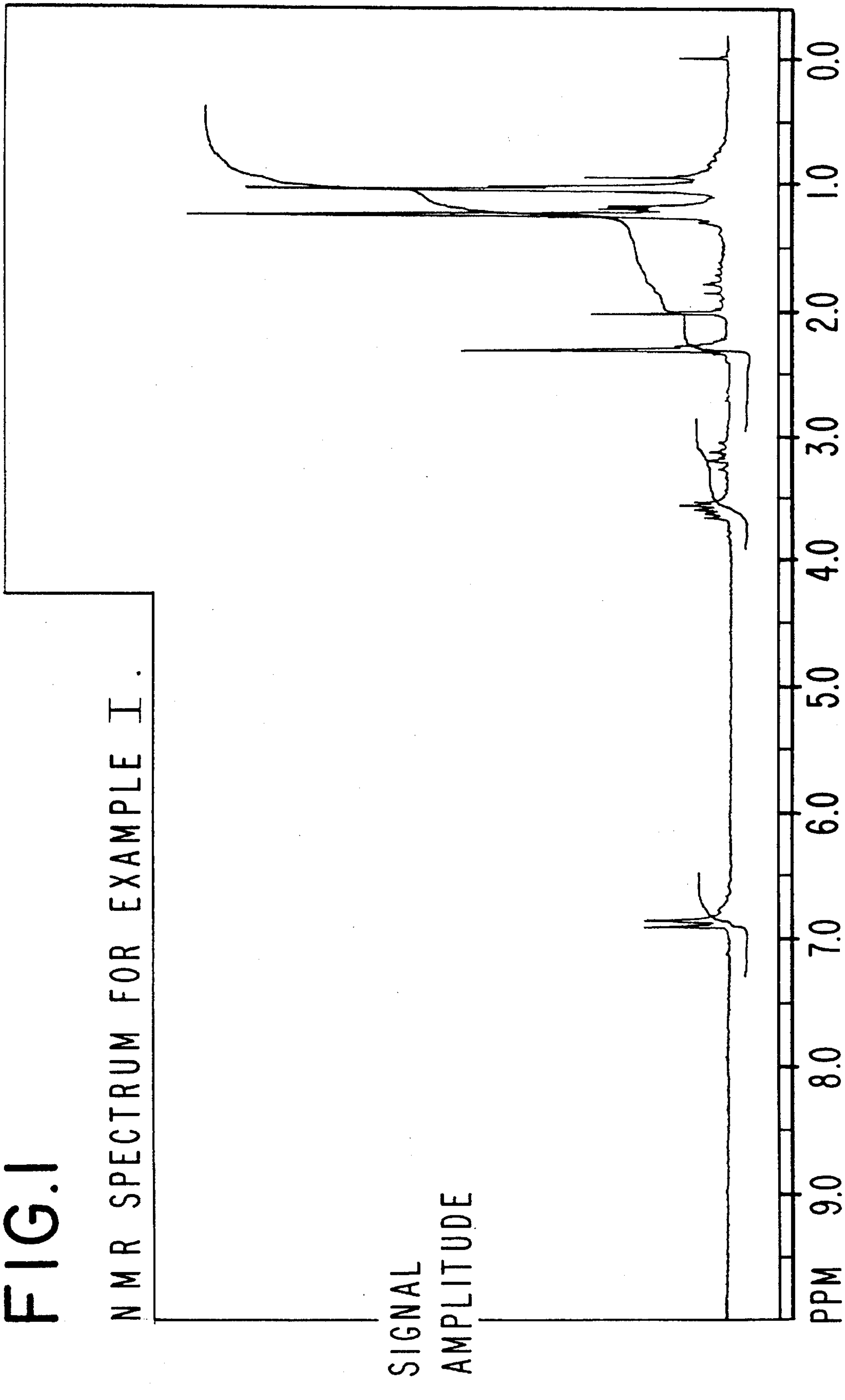
FIG. 1 is the NMR spectrum for the compound having the structure.

FIG. 1 is the NMR spectrum for the resulting mixture having the structure:

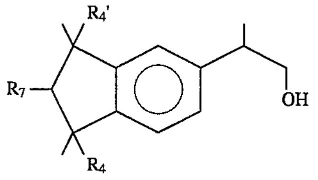

EXAMPLE II PREPARATION OF CHLORINATED REARRANGEMENT PRODUCT OF METHYL GALAXOLID® ALCOHOL

Reaction:

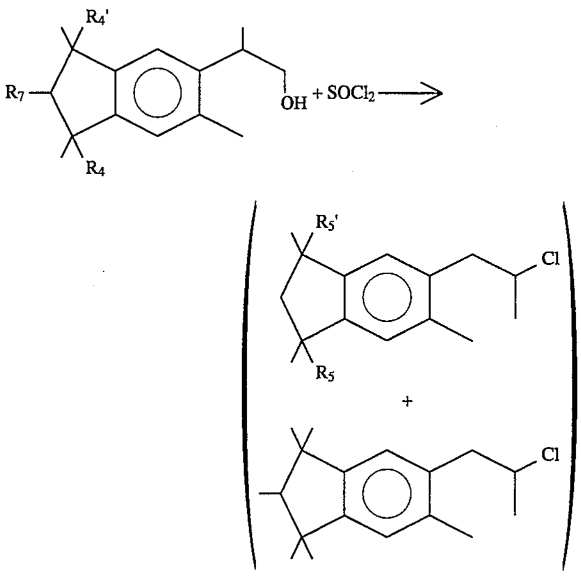

wherein in the structure:

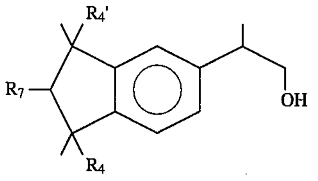

this structure represents a mixture wherein in the mixture in one of the compounds $R_4$ and $R_4'$ are both methyl and $R_7$ is methyl (90% of the mixture) and in the other compounds one of $R_4$ or $R_4'$ is methyl and the other is ethyl and $R_7$ is hydrogen (10% by weight of the mixture) and in the structure:

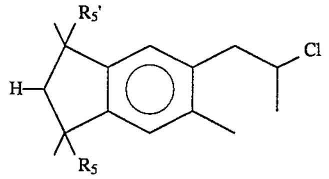

this structure represents a 50:50 mixture wherein in one of the components of the mixture, $R_5$ is methyl and $R_5'$ is ethyl and in the other of the components of the mixture, $R_5'$ is methyl and $R_5$ is ethyl.

Into a 2 liter reaction vessel equipped with stirrer, thermometer, reflux condenser and addition funnel, also equipped with ice bath are placed 350 grams of the mixture of compounds defined according to the structure:

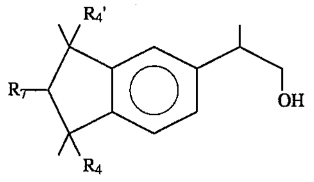

prepared according to Example I, dissolved in 350 ml of methylene chloride. The methylene chloride-methyl GALAXOLIDE® alcohol mixture is stirred at 25° C. for a period of 0.5 hours. Over a period of two hours, using the cooling bath, 238 grams of thionyl chloride is added to the reaction mass with stirring.

At the end of the two hour addition period, the reaction mass is stirred for a period of 0.5 hours maintaining the temperature thereof at 25° C.

10 Grams of titanium tetrachloride is then added to the reaction mass and the reaction mass is stirred at 25° C. for an additional two hour period.

The reaction mass is then quenched on ice and washed with an equal volume of sodium carbonate (saturated aqueous solution). The organic phase is separated from the aqueous phase and the organic phase is dried over anhydrous magnesium sulfate.

The organic phase is then fractionally distilled on a Goodloe column yielding the following fractions:

| Fraction Number | Vapor Temperature (°C.) | Liquid Temperature (°C.) | Vacuum mm/Hg. Pressure |
|---|---|---|---|
| 1 | 23/165 | 23/175 | 10/3 |
| 2 | 162 | 175 | 3 |
| 3 | 167 | 180 | 3 |
| 4 | 167 | 165 | 2 |
| 5 | 170 | 220 | 4 |

The resulting product is a mixture of compounds defined according to the structure:

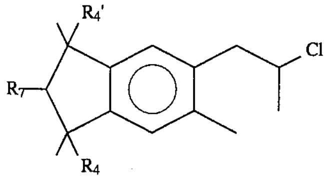

This represents a mixture of compounds wherein, in the mixture in one of the compounds $R_4$ and $R_4'$ are both methyl and $R_7$ is methyl (90% by weight of the compounds) and in the other compounds one of $R_4$ or $R_4'$ is methyl and the other is ethyl and $R_7$ is hydrogen (10% by weight of the mixture of compounds). FIG. 2 is the GLC profile of the reaction product. The peak indicated by reference numeral 21 is the peak for the mixture of compounds having the structure:

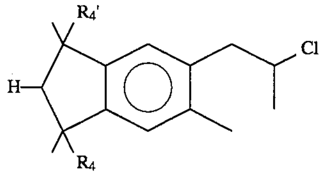

wherein, in the mixture one of $R_5$ or $R_5'$ is methyl and the other is ethyl. The peak indicated by reference numeral 23 is the peak for the pure compound having the structure:

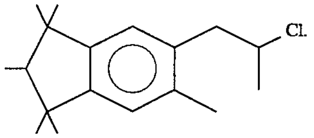

The resulting product has an intense natural woody, natural musky aroma with pleasant natural animalic topnotes.

FIG. 3 is the NMR spectrum for the mixture of compounds having the structure:

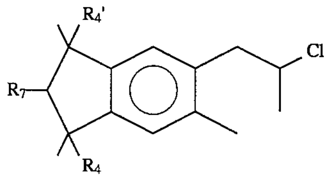

EXAMPLE III PREPARATION OF METHYL ETHER DERIVATIVE OF REARRANGEMENT PRODUCT OF METHYL GALAXOLIDE® LCOHOI,

Reaction:

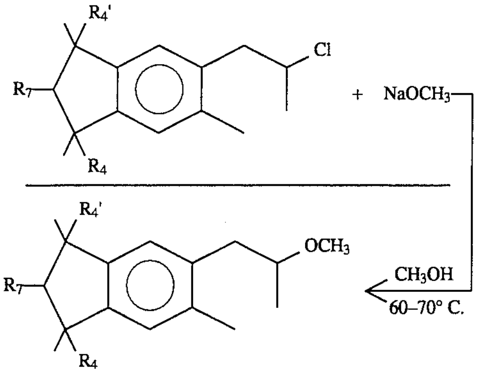

wherein, in the representation of the structures:

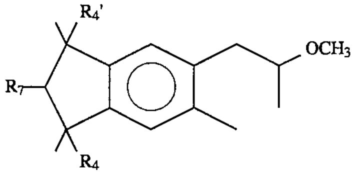

and

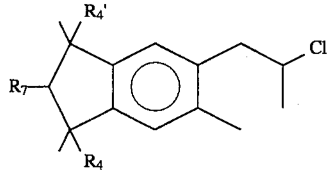

in each of the mixtures in one of the compounds $R_4$ and $R_4'$ are both methyl and $R_7$ is methyl (90% by weight of the mixture) and in the other compounds one of $R_4$ or $R_4'$ is methyl and the other is ethyl and $R_7$ is hydrogen (10% by weight of the mixture of compounds).

Into a 1 liter reaction vessel equipped with stirrer, thermometer, reflux condenser and addition funnel are placed 100 grams of the mixture of compounds defined according to the structure:

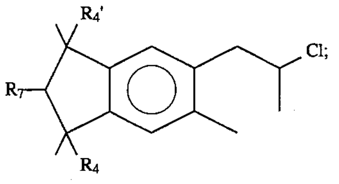

400 grams of methyl alcohol; and 100 grams of sodium methoxide. The reaction mass is heated to reflux (60°–70° C.) and maintained at reflux for a period of two hours. At the end of the two hour period, the reaction mass is cooled to room temperature. The reaction mass is then washed with an equal volume of 10% dilute acetic acid. The reaction mass is then washed again with four equal volumes of saturated aqueous sodium chloride. The reaction mass is then dried over anhydrous magnesium sulfate and fractionally distilled yielding the mixture of compounds defined according to the structure:

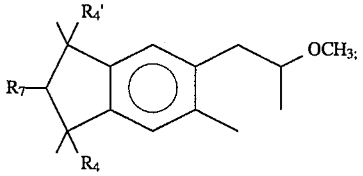

wherein, the mixture in one of the compounds $R_4$ and $R_4'$ are both methyl and $R_7$ is methyl (90% by weight of the mixture) and in the other compounds one of $R_4$ or $R_4'$ is methyl and the other is ethyl and $R_7$ is hydrogen (10% by weight of the mixture of compounds).

FIG. 4 is the NMR spectrum for the mixture of compounds defined according to the structure:

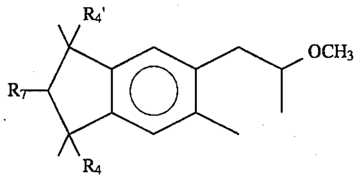

The resulting product has a novel natural musk, rose-like aroma with intense and substantive green undertones and lilac topnotes.

EXAMPLE IV

MUSK PERFUME

The following musk perfume is prepared:

| Ingredients | Parts by Weight | | |
|---|---|---|---|
| | Example IV (A) | Example IV (B) | Example IV (C) |
| The compound having the structure: 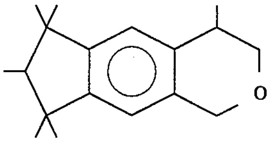 | 32 | 32 | 32 |
| The compound having the structure: 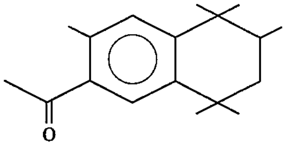 | 32 | 32 | 32 |
| The compound having the structure: 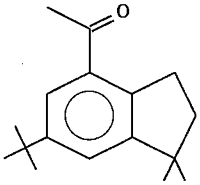 | 16 | 16 | 16 |
| The compound having the structure: 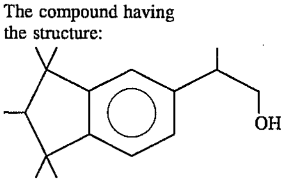 | 4 | 4 | 4 |
| Mixture of compounds having the structure: 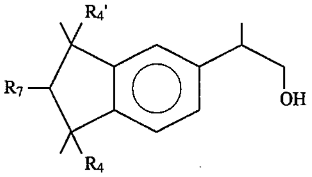 | 20 | 0 | 0 |
| Mixture of compounds having | 0 | 20 | 0 |

-continued

| Ingredients | Parts by Weight Example IV (A) | Example IV (B) | Example IV (C) |
|---|---|---|---|
| the structure: 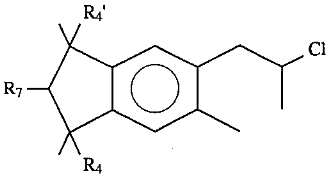 | | | |
| Mixture of compounds having the structure: 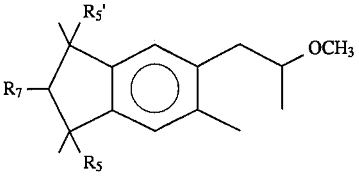 | 0 | 0 | 20 |

The mixture of compounds having the structure:

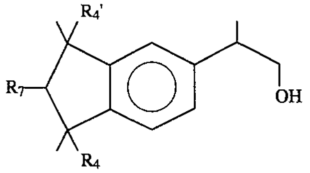

imparts to this musk formulation a natural and intense sweet animalic undertone. Accordingly, the resulting perfume composition of Example IV(A) can be described as "musky with sweet animalic undertones".

The mixture of compounds defined according to the structure:

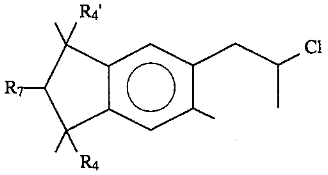

imparts to this musk perfume intense natural woody undertones and natural animalic topnotes. Accordingly, the perfume composition of Example IV(B) can be described as "intense substantive natural musky with woody undertones and natural animalic topnotes".

The mixture of compounds defined according to the structure:

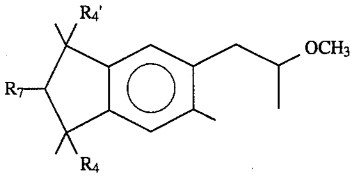

imparts to the musk formulation natural musky nuances, rose undertones, green undertones and lilac topnotes. Accordingly, the perfume composition of Example IV(C) can be described as "natural musky with rose and green undertones and lilac topnotes".

EXAMPLE V

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below.

TABLE II

| Ingredients | Aroma Description |
|---|---|
| Mixture of compounds defined according to the structure: 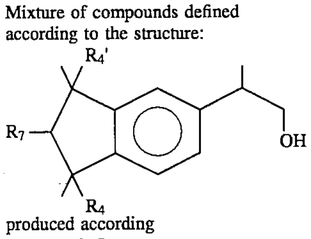 produced according to Example I. | An intense natural musky aroma. |
| Mixture of compounds defined according to the structure: 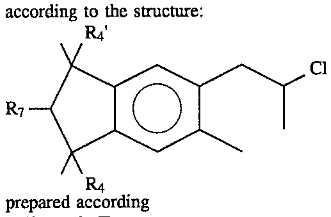 prepared according to Example II. | An intense, natural woody natural aroma with pleasant natural animalic topnotes. |
| Mixture of compounds defined according to the structure: 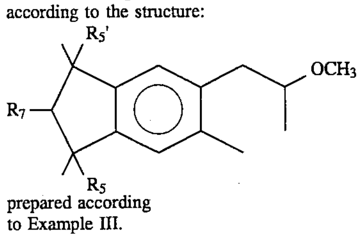 prepared according to Example III. | An intense natural musk, animalic aroma with a cigar-box-like topnotes and early morning forest path undertones. |

TABLE II-continued

| Ingredients | Aroma Description |
|---|---|
| 3% Mixture of compounds defined according to the structure: 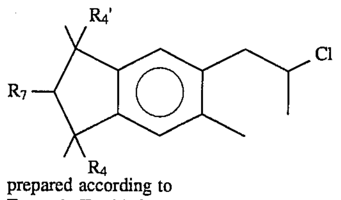 prepared according to Example II with 97% by weight of the compound having the structure: 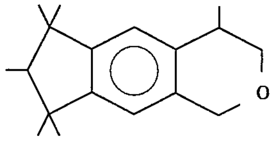 | An intense powdery sweet natural musk aroma with woody topnotes. |
| 3% Mixture of compounds defined according to the structure: 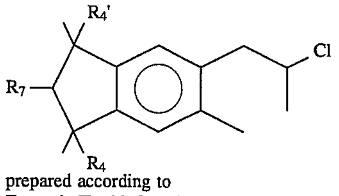 prepared according to Example II with 97% by weight of the compound having the structure: 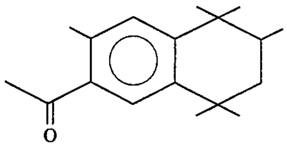 | An intense powdery sweet natural musk with animalic topnotes. |
| 7% Mixture of compounds defined according to the structure: 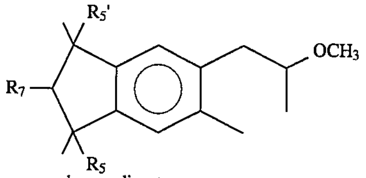 prepared according to Example II with 97% by weight of the compound having the structure: 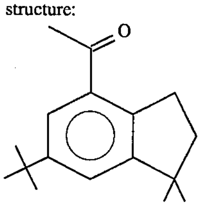 | An intense powdery sweet natural musk aroma with woody, mahogany, green undertones and faint lilac topnotes. |
| Perfume composition of Example IV (A). | Musky with sweet animalic undertones. |
| Perfume composition of Example IV (B). | Intense substantive natural musky with woody undertones and natural animalic topnotes. |
| Perfume Composition of Example IV (C). | Natural musky with rose and green undertones and lilac topnotes. |

EXAMPLE VI

PERFUMED LIQUID DETERGENTS

Concentrated liquid detergents (Lysine salt of n-dodecylbenzene sulfonic acid as more specifically described in U.S. Pat. No. 3,948,818 issued on Apr. 6, 1976) with aroma nuances as set forth in Table II of Example V are prepared containing 0.10%, 0.15%, 0.20%, 0.25%, 0.30% and 0.35% of the substance set forth in Table II of Example V. They are prepared by adding and homogeneously mixing the appropriate quantity of substance set forth in Table II of Example V in the liquid detergent. The detergents all possess excellent aromas as set forth in Table II of Example V, the intensity increasing with greater concentrations of substance as set forth in Table II of Example V.

EXAMPLE VII

PREPARATION OF COLOGNES AND HANDKERCHIEF PERFUMES

Compositions as set forth in Table II of Example V are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example V are imparted to the colognes and to the handkerchief perfumes at all levels indicated.

EXAMPLE VII I

PREPARATION OF SOAP COMPOSITIONS

One hundred grams of soap chips [per sample] (IVORY® , produced by the Procter & Gamble company of Cincinnati, Ohio), are each mixed with one gram samples of substances as set forth in Table II of Example V until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example V.

EXAMPLE IX

PREPARATION OF SOLID DETERGENT COMPOSITIONS

Detergents are prepared using the following ingredients according to Example I of Canadian Patent No. 1,007,948:

| Ingredient | Percent by Weight |
|---|---|
| "NEODOL ®" 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosophate-free detergent. Samples of 100 grams each of this detergent are admixed with 0.10, 0.15, 0.20 and 0.25 grams of each of the substances as set forth in Table II of Example V. Each of the detergent samples has an excellent aroma as indicated in Table II of Example V.

EXAMPLE X

Utilizing the procedure of Example I at column 15 of U.S. Pat. No. 3,362,396, non-woven cloth substrates useful as drier-added fabric softening articles of manufacture are prepared wherein the substrate, the substrate coating and the outer coating and the perfuming material are as follows:

1. A water "dissolvable" paper ( "Dissolvo Paper");
2. Adogen 448 (m.p. about 140° F.) as the substrate coating; and
3. An outer coating having the following formulation (m.p. about 150° F.):

| | |
|---|---|
| 58% | $C_{20-22}$ HAPS |
| 22% | isopropyl alcohol |
| 20% | antistatic agent |
| 1% | of one of the substances as set forth in Table II of Example V. |

Fabric softening compositions prepared according to Example I at column 15 of U.S. Pat. No. 3,632,396 having aroma characteristics as set forth in Table II of Example V, consist of a substrate coating having a weight of about 3 grams per 100 square inches of substrate; a first coating on the substrate coating consisting of about 1.85 grams per 100 square inches of substrate and an outer coating coated on the first coating consisting of about 1.4 grams per 100 square inches of substrate. One of the substances of Table II of Example V is admixed in each case with the outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table II of Example V.

EXAMPLE XI

HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% food grade ethanol, 8.0 grams of the polymer is dissolved in the alcohol. The following ingredients are added to the PVP/VA alcoholic solution:

| Ingredient | Percent by Weight |
|---|---|
| Dioctyl sebacate | 0.05 |
| Benzyl alcohol | 0.10 |
| Dow Corning 473 fluid (prepared by the Dow Corning Corporation | 0.10 |
| Tween 20 Surfactant (prepared by I.C.I. America Corporation | 0.03 |
| One of the perfumery substances as set forth In Table II of Example V | 0.10 |

The perfuming substances as set forth in Table II of Example V add aroma characteristics as set forth in Table II of Example V which are rather intense and aesthetically pleasing to the users of the soft-feel, good-hold pump hair sprays.

EXAMPLE XII

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of the Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.) .

GAFQUAT® 755N polymer (manufactured by the GAF Corporation of 140 West 51st Street, New York, N.Y.) (5.0 weight percent) is admixed with 0.1 weight percent sodium sulfite and 1.4 weight percent polyethylene glycol 6000 distearate produced by the Armak Corporation.

The resulting material is then mixed and cooled to 45° C. and 0.3 weight percent of perfuming substance as set forth in Table II of Example V is added to the mixture. The resulting mixture is cooled to 40° C. and blending is carried out for an additional one hour in each case. At the end of this blending period, the resulting material has a pleasant fragrance as indicated in Table II of Example V.

What is claimed is:

1. At least one methyl, substituted propyl-substituted pentamethyl indane derivative defined according to the structure:

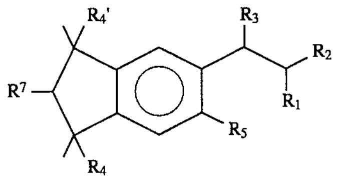

wherein $R_1$ is represents hydroxyl or methyl; $R_2$ represents hydrogen, chloro or $OR_6$ and $R_3$ represents hydrogen or methyl with the provisos:

(i) when $R_1$ is hydroxyl, $R_2$ is hydrogen and $R_3$ is methyl; and (ii) when $R_1$ is methyl, $R_2$ is chloro or $OR_6$ and $R_3$ is hydrogen wherein $R_6$ is methyl, ethyl, n-propyl or i-propyl and wherein the structure represents a mixture wherein, in the mixture in one of the compounds $R_4$ and $R_4'$ are both methyl and $R_7$ is methyl; and in the other compounds one of $R_4$ or $R_4'$ is methyl and the other is ethyl and $R_7$ is hydrogen.

2. A substance of claim 1 defined according to the structure:

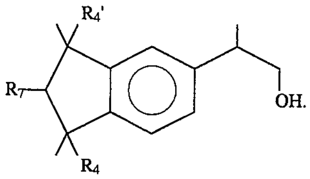

3. A substance of claim 1 defined according to the structure:

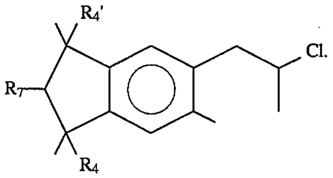

4. A substance of claim 1 defined according to the structure:

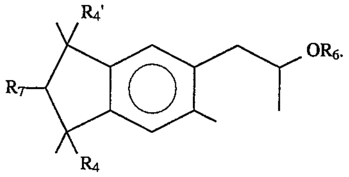

5. A substance of claim 1 defined according to the structure:

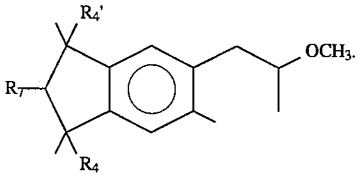

6. A mixture containing from 1–10% of the substance of claim 1 and from 99–90% of a musk chemical selected from the group consisting of chemicals having the structures:

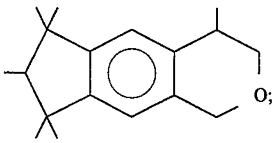

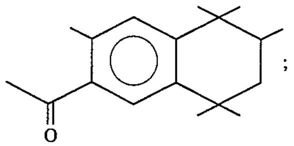

-continued

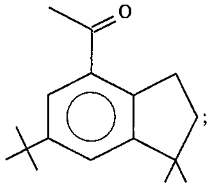

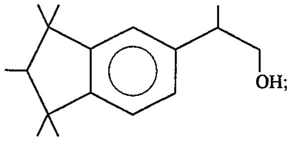

and

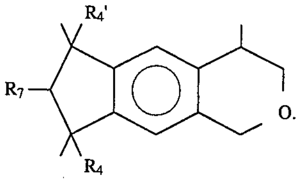

7. A mixture containing from 1–10% of the substance defined according to claim 3 and from 99–90% of a musk chemical selected from the group consisting of chemicals having the structures:

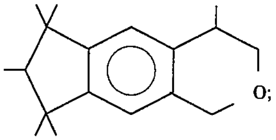

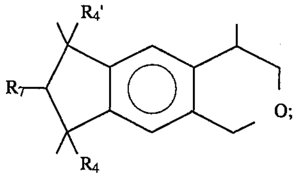

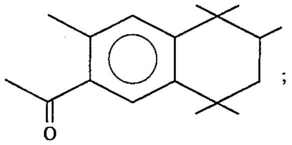

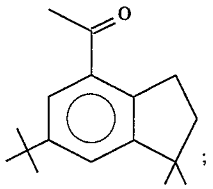

and

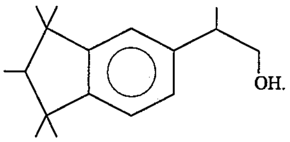

8. A process for augmenting, enhancing or imparting an aroma to or in a perfume composition, a cologne or a perfumed article comprising the step of intimately admixing with said perfume composition, cologne or perfumed article an aroma augmenting, enhancing or imparting quantity of at least one methyl, substituted propyl-substituted pentamethyl indane derivative defined according to claim 1.

9. A process for augmenting, enhancing or imparting an aroma in or to a perfume composition, perfumed article or cologne comprising the step of intimately admixing with a perfume composition, cologne or perfumed article base an aroma augmenting, enhancing or imparting quantity of a substance defined according to claim 3.

10. A process for augmenting, enhancing or imparting an aroma in or to a perfume composition, perfumed article or cologne comprising the step of intimately admixing with a perfume composition, cologne or perfumed article base an aroma augmenting, enhancing or imparting quantity of a substance defined according to claim 6.

11. A perfume composition comprising a perfume base and intimately admixed therewith an aroma imparting, augmenting or enhancing quantity of at least one methyl, substituted propyl-substituted pentamethyl indane derivative defined according to claim 1.

12. A perfume composition comprising a perfume base and intimately admixed therewith an aroma imparting, augmenting or enhancing quantity of at least one methyl, substituted propyl-substituted pentamethyl indane derivative defined according to claim 3.

13. A perfume composition comprising a perfume base and intimately admixed therewith an aroma imparting, augmenting or enhancing quantity of at least one methyl, substituted propyl-substituted pentamethyl indane derivative defined according to claim 6.

14. A cologne comprising water, ethanol and an aroma imparting quantity of at least one methyl, substituted propyl-substituted pentamethyl indane derivative defined according to claim 1.

15. A cologne comprising water, ethanol and an aroma imparting quantity of at least one methyl, substituted propyl-substituted pentamethyl indane derivative defined according to claim 3.

16. A cologne comprising water, ethanol and an aroma imparting quantity of at least one methyl, substituted propyl-substituted pentamethyl indane derivative defined according to claim 6.

17. A perfumed polymer comprising a microporous polymer and contained in the interstices thereof at least one methyl, substituted propyl-substituted pentamethyl indane derivative defined according to claim 1.

18. A perfumed polymer comprising a microporous polymer and contained in the interstices thereof at least one methyl, substituted propyl-substituted pentamethyl indane derivative defined according to claim 3.

19. A perfumed polymer comprising a microporous polymer and contained in the interstices thereof at least one methyl, substituted propyl-substituted pentamethyl indane derivative defined according to claim 6.

* * * * *